United States Patent [19]

Sutherland et al.

[11] Patent Number: 5,061,236

[45] Date of Patent: Oct. 29, 1991

[54] VENOUS RESERVOIR WITH IMPROVED INLET CONFIGURATION AND INTEGRAL SCREEN FOR BUBBLE REMOVAL

[75] Inventors: Karl M. Sutherland, Laguna Hills; William R. Patterson, Long Beach, both of Calif.

[73] Assignee: Baxter International Inc., Deerfield, Ill.

[21] Appl. No.: 554,759

[22] Filed: Jul. 16, 1990

[51] Int. Cl.⁵ .......... A61M 1/00

[52] U.S. Cl. .......... 604/4; 604/410; 604/122; 422/310; 210/436

[58] Field of Search .......... 604/403-416, 604/4, 122, 126; 422/310, 47, 48; 210/436, 472

[56] References Cited

U.S. PATENT DOCUMENTS

| | | | |
|---|---|---|---|
| 3,985,135 | 10/1976 | Carpenter et al. | 604/410 |
| 4,396,383 | 8/1983 | Hart | 604/410 X |
| 4,576,603 | 3/1986 | Moss | 604/410 |
| 4,602,910 | 7/1986 | Larkin | 604/87 |
| 4,734,269 | 3/1988 | Clarke et al. | 604/405 X |
| 4,863,452 | 9/1989 | Irmiter et al. | 604/122 X |

*Primary Examiner*—Robert A. Hafer
*Assistant Examiner*—Kerry Owens
*Attorney, Agent, or Firm*—Robert D. Buyan; Bruce M. Canter

[57] ABSTRACT

A blood reservoir device comprising a generally flexible blood collection chamber having an inlet portion and a main portion. The inlet portion is preferably sized and configured such that blood entering the inlet portion will avoid turbulence and will undergo generally laminar flow through the inlet portion, into the main portion of the chamber. A vent tube is provided for venting coalesced or collected gas bubbles from the top edge of the chamber. Additionally, one or more filter elements may be positioned within the chamber to further facilitate removal of air bubbles from blood passing through the chamber.

15 Claims, 3 Drawing Sheets

12
14
30
12
14

10
64
18
70
64
40
42
54
FROM CARDIOTOMY RESERVOIR
44
48
52
FROM RIGHT ATRIUM
50
46
56
64
16
16
X
Y
24
70
24
36
28
16
18
64
16
72
68
66
75
AIR OUT
24
16
16
22
18
64
64
60
TO OXYGENATOR 30 28

28

64c
64b
64c
14
64c
64b
64b
76
64b
6
6
28
73
66
68
74
64b
5
5
64a
12
64a
41
40
64a
64a
64a
64a
61
60

VENOUS RESERVOIR WITH IMPROVED INLET CONFIGURATION AND INTEGRAL SCREEN FOR BUBBLE REMOVAL

FIELD OF THE INVENTION

The present invention relates generally to biomedical equipment and more particularly to an improved venous reservoir for use in extracorporeal blood oxygenation systems.

BACKGROUND OF THE INVENTION

In many cardiovascular surgical procedures, and some nonsurgical therapeutic/supportive procedures, cardiopulmonary bypass systems are utilized to accomplish blood oxygenation and circulatory support while normal cardiopulmonary function of a patient is interrupted or impaired. Basically, the typical cardiopulmonary bypass systems of the prior art comprises (a) a venous reservoir for pooling and collecting venous return blood, (b) a pump for circulating the venous return blood and (c) an oxygenation device for oxygenating venous return blood prior to reinfusion of the blood into the vasculature of the patient. Additionally, cardiopulmonary bypass systems which are utilized during cardiothoracic surgical procedures typically incorporate an additional cardiotomy reservoir/filter component wherein blood suctioned from the operative site is collected, filtered and shunted into the above-mentioned venous reservoir wherein the filtered cardiotomy blood is combined with the venous return blood for subsequent pumping, oxygenation and return to the patient. Such cardiotomy reservoir/filter component is often fluidly attached to the venous blood accumulator or reservoir such that the venous blood accumulator or reservoir will receive and hold the filtered cardiotomy blood in combination or admixture with venous return blood received from the right heart or vena cava of the patient.

The venous blood accumulator or "venous reservoir" commonly consists of either a flexible bag or hard shell vessel having a blood inlet for receiving an inflow of blood, and a blood outlet for subsequent outflow of blood into the attendant portions of the bypass system (e.g. into the pump and/or membrane oxygenator). In surgical applications wherein the above-described cardiotomy reservoir component is employed, the blood inlet of the venous reservoir receives a mixture of (a) venous return blood obtained directly from the right atrium or vena cava of the patient, and (b) filtered cardiotomy blood which has been suctioned from the operative sight and preprocessed (e.g. filtered and defoamed) in the separate cardiotomy reservoir/filter.

The venous reservoir is desirably adapted to accommodate fluctuations in pooled blood volume brought about by relative variations in the rate of blood inflow (e.g. changes in venous return or cardiotomy blood volume) and/or the rate of blood outflow (e.g. changes in the rate of the bypass system pump). One means of accommodating such fluctuations in pooled blood volume is to provide a flexible bag-like venous reservoir which is capable of expanding and contracting in accordance with the normal variations in pooled blood volume with the reservoir.

Flexible bag-type venous reservoirs of the prior art are described in U.S. Pat. No. 4,493,705 (GORDON ET AL), U.S. Pat. No. 4,643,713 (VIITALA), U.S. Pat. No. 4,734,269 (CLARKE ET AL), U.S. Pat. No. 4,795,457 (COONEY) and U.S. Pat. No. 4,863,452 (IRMITER ET AL). Additionally, other types of venous return reservoirs (e.g. rigid, hard shell reservoirs) are described in U.S. Pat. No. 4,698,207 (BRINGHAM ET AL), U.S. Pat. No. 4,737,139 (ZUPKAS ET AL) and U.S. Pat. No. 4,756,705 (BEIJBOM ET AL).

The flexible bag-type venous reservoirs of the prior art have assumed various shapes and configurations and have incorporated various filters and vent tubes for removing bubbles or entrained air from the blood. For example, U.S. Pat. No. 4,493,705 describes a bag-type venous reservoir which is formed in an inverted "U" shape such that bubbles Within the blood may rise to the upper most point of the inverted "U" configuration, and be subsequently vented therefrom by way of an attendant vent port. Also, a filter screen is positioned near the midpoint of the "U" shaped bag to facilitate removal of air bubbles from the blood. Others of the flexible bag-type venous reservoirs have utilized various different shapes, configurations and filter elements to facilitate trapping and removal of entrained bubbles from return blood passing therethrough.

Because none of the venous reservoirs of the prior art have proven to provide consistently optimal bubble removal and/or optimal flow performance in all applications, there remains a need in the art for further improvements and refinements in the configuration, construction and function of such venous reservoirs.

SUMMARY OF THE INVENTION

In accordance with the invention there is provided a blood reservoir device comprising a generally flexible blood collection chamber having an inlet portion and a main portion. The inlet portion of the chamber is fluidly connected to the main portion of the chamber such that blood may pass from the inlet portion into the main portion. A blood inflow tube is fluidly connected to the inlet portion of the blood collection chamber and an outflow tube is fluidly connected to the main portion of the blood collection chamber, such that blood may enter the inlet portion, subsequently pass into the main portion and finally exit the collection chamber through the outflow tube situated in the main portion of the chamber. At least one air vent tube is fluidly connected to the blood collection chamber to permit continuous or periodic venting of air therefrom.

Further in accordance with the invention, the inlet portion of the collection chamber is configured so as to minimize or eliminate turbulence and/or eddy formation as blood flows into the inlet portion of the chamber (i.e. flow remains generally laminar in the inlet portion of the chamber). This may be accomplished by providing an inlet portion of the chamber which is substantially smaller in volume than the secondary or "main" chamber portion. Also, the inlet portion of the chamber may be configured so as to gradually increase in diameter or cross-section area, thereby avoiding direct flow of blood from the inflow tube into a large existing pooled quantity of blood.

Still further in accordance with the invention, the inlet portion of the chamber may be sized and configured so as to hold a smaller volume of blood than the main portion. This resultant minimization of blood volume within the inlet portion will serve to minimize turbulent mixing or eddy formation within the reservoir as may occur when blood flows directly from a generally small diameter inlet tube into a blood filled reservoir of large volume (e.g., the main portion) without attendant dampening, baffling or flow control elements.

Still further in accordance with the invention, a filter element, such as a screen or soft mesh material, may be positioned within the collection chamber to capture and/or filter air bubbles from the blood as it passes through the chamber. Such filter element may be positioned within the main portion of the chamber such that blood passing from the inlet portion into the main portion will necessarily pass through the filter element, thereby facilitating removal of air bubbles from the blood, before the blood exits the main chamber. The filter element may be made of any appropriate filtering material such as soft mesh, screen, fabric or other material. It is desirable that the pore or mesh size be between 20 and 200 microns and preferably about 105 microns.

Still further in accordance with the invention, the blood collection chamber may be configured such that the top of the chamber is peaked or curved, thereby providing a "high point" adjacent the vent tube. Thus, coalesced bubbles and gas collecting at the high point of the chamber may be continuously or periodically vented from the chamber, through the vent tube.

Further objects and advantages of the invention will become apparent to those skilled in the art upon reading and understanding of the following detailed description and the accompanying drawings.

Figure 3:
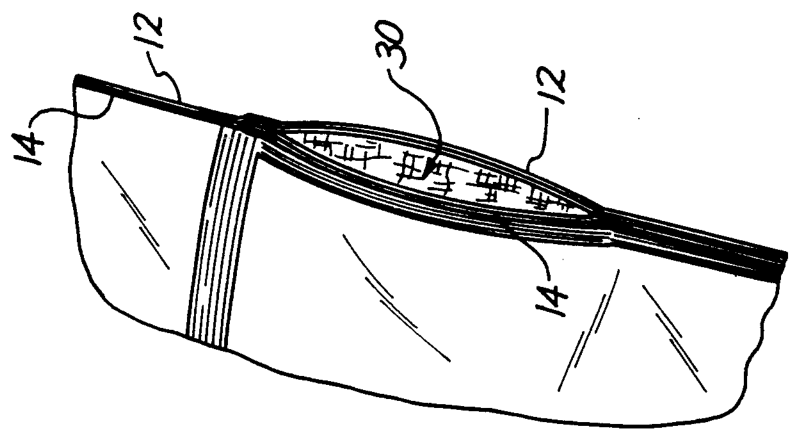
FIG. 3 is a partial cross-sectional view through line A—A' of FIG. 2.

DETAILED DESCRIPTION OF AN ILLUSTRATIVE EMBODIMENT i. Structure of the Illustrated Embodiment

The following detailed description and the accompanying drawings are provided for purposes of describing one (1) embodiment of the present invention and are not intended to limit the scope of the invention in any way.

Referring now to the drawings, the embodiment shown comprises a flexible bag-like venous reservoir 10. Such venous reservoir 10 is formed of first 12 and second 14 sheets of thin plastic material (e.g. polyvinyl chloride PVC) sheet having a thickness of about 0.005 in.–0.060 in. and preferably 0.020 in. each. The first 12 and second 14 sheets are situated in surface to surface juxtaposition and are fused or attached to one another along selected boundaries 16, 18. Such fusing or attachment of the first sheet 12 to the second sheet 14 may be achieved by any suitable means, including heat sealing or radio frequency welding.

The fusion or attachment of the first sheet 12 to the second sheet 14 along inner boundary 16 defines therewithin an expandable blood collecting space or chamber 22. The sealing of the first sheet 12 to the second sheet 14 along the outer boundaries 18 defines and forms a sealed outer periphery on the bag and non-blood-receiving region 24, between the outer boundary 18 and the inner boundary 16.

The chamber 22 is configured so as to facilitate efficient and complete removal of air bubbles from the blood while avoiding unnecessary turbulence or eddy current formation. In the embodiment shown (FIGS. 1–4), the chamber 22 is divided into a first inlet portion 70 and a second main region or main chamber 72.

A porous filter 28 or screen is positioned within the main chamber 72. The filter 28 or screen may be made of any material capable of screening or filtering out air bubbles or other foreign matter from blood passing therethrough. In the embodiment shown in FIGS. 1–4, the filter 28 is formed of a soft mesh material, such as polyester or dacron mesh. The filter has a multiplicity of apertures, pores, mesh openings or fluid passageways being about 20–200 microns in width or diameter and preferably about 105 microns.

The filter 28 may be fixed within the reservoir 10 by any suitable means. In the embodiment shown, the filter 28 is fixed in place by heat sealing along inner boundary 16, except for the seam 36 along open mouth 30. The filter 28, thus assumes a bag-like configuration whereby blood may flow into the filter 28 freely through the open mouth 30, but, thereafter, must pass through the mesh of the bag-like filter 28 before flowing out of the venous outlet 60.

The edges of the bag-like filter element 28, adjacent the open mouth 30, are separately attached to the first 12 and second 14 sheets respectively, as shown in FIG. 3.

A blood inlet tube 40 is partially inserted into, and sealed within, bottom of the inlet 70 of the reservoir 10. In a preferred embodiment, the blood inlet tube 40 is approximately ½ inch in diameter. The blood inlet tube 40 may be connected to a "Y" adaptor 42, as shown. The "Y" adaptor 42 has cardiotomy blood inlet arm 44 and a venous return blood input arm 46. Cardiotomy blood inlet arm 44 is fluidly connectable to an attendant cardiotomy filtering device to provide a continuous or intermittent flow of filtered cardiotomy blood into the blood inlet tube 40.

The venous blood inlet arm 46 is connectable to the right heart or vena cava of the patient to provide an inflow of venous return blood from the patients body. An extension tube 48 and sampling fitting 50 may be positioned on the venous blood inlet arm 48. The sampling fitting 50 may comprise a Leur-adapted sampling port 52 configured to permit periodic sampling of the venous return blood by a standard disposable syringe.

Similarly, sampling ports 54 and 56 may be provided on opposite sides of the "Y" adaptor 42 to permit sampling of the blood mixture (i.e. cardiotomy blood plus venous return blood) passing into the venous inlet 40.

The inlet portion 70 of the chamber 22 extends from the mouth of the venous inlet tube 40 to the mouth 30 of the bag-like filter 28. The inlet 70 becomes progressively greater in cross-sectional area as it extends from its base x to its top edge y. Such increase in cross-sectional area facilitates relatively laminar flow of blood into the inlet 70 and avoids or minimizes turbulence or eddy current formation as may be caused by direct infusion of blood into a large pooled reservoir of blood (e.g. as may be caused by direct infusion of blood into the main portion 72 of the chamber 22). Such configuration of the inlet portion 70, and the resultant relatively laminar flow of blood within the inlet, facilitates separation and rising of air bubbles within the blood, such that the air bubbles will rise, or begin to rise, to the top of the inlet 70 before the blood passes into the main chamber 72. Also, by avoiding or minimizing turbulence, the inlet 70 configuration minimizes the potential that any entrained air bubbles will become broken up or dispersed within the blood. In the embodiment shown in FIGS. 1–4, the cross-sectional area of the inlet 70 increases from the base x to the top edge y at a rate of approximately 0.4 $in^2/in$. For example, in the embodiment shown, the length of the inlet 70 is approximately 4½ inches from base x to upper edge y. The cross-sectional area at the base x is approximately 0.2 square inches and the cross-sectional area at the top edge y is approximately 2.0 square inches.

It is preferable that the inlet 70 be configured generally as a cone, skewed cone, or generally straight and/or curved chamber of elliptical or ovoid cross-section. The inlet 70 is shown narrowest at its base X and which becomes progressively wider from its base to an end Y generally opposite its base. The increase in cross-sectional area from base X to tope end Y is relatively constant over the length of the inlet 70 so as to avoid unnecessarily rapid or regionalized fluctuations in blood inlet pressure, or the occurrence of turbulence or eddy formation as may occur if blood rapidly impinges or flows into a body or pool of existing blood. Such does not, however, preclude the inlet 70 from being configured with gradual outward curvatures of the side edges (e.g. a curved venturi configuration).

A plurality of apertures 64 are formed at various locations around the periphery of the reservoir 10 so as to permit the reservoir 10 to be held in a fixed position by a plurality of hangers or pins extending from an attendant reservoir support structure. The hangers or pins will pass through each of the apertures 64 so as to hold the reservoir 10 in a fully operative position, without undesirable folds or creases therein.

A standpipe or air vent tube 66 passes downwardly between the first 12 and second 14 sheets such that the bottom end 68 of the air vent tube 66 passes through aperture 73 into the bag-like filter 28 and terminates just below the upper edge of inner boundary 16. The air vent tube 66 is heat sealed or otherwise sealed between sheets 12 and 14 so as to hold the tube 66 in place and to prevent any substantial leakage of gas around the tube 66. A stop cock 75 may be positioned on the upper end of the air vent tube 66 so as to permit periodic and/or continuous venting of air through the tube 66.

ii. Assembly of the Illustrated Embodiment

Figure 4:
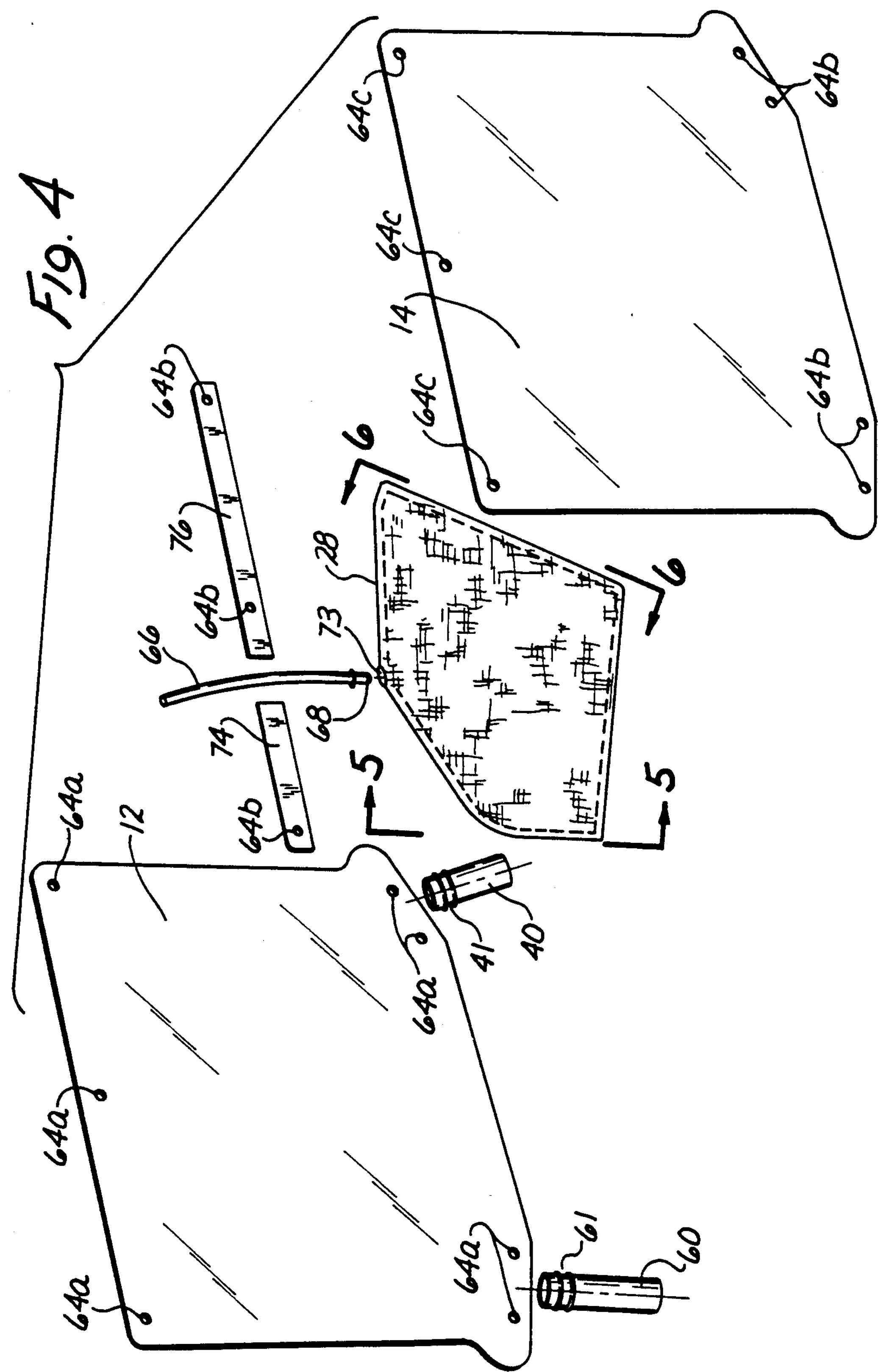
FIG. 4 is an exploded view of a venous reservoir of the present invention.

As may be appreciated from the exploded view of FIG. 4, the bottom end 68 of the tube 66 is initially inserted into a hole 72 formed in the top of the bag-like filter 28. First 74 and second 76 reinforcement strips made of pliable plastic or other reinforcement material, are positioned in horizontal juxtaposition to the upper edge of the first sheet 12 such that the apertures *64b* of the reinforcement strips 74, 76 are aligned with the apertures *64a* of the first sheet. The reinforcement strips provides some additional longitudinal rigidity along the upper edge of the reservoir bag 10 and also helps to prevent tearing of the apertures 64 located along such upper edge of the reservoir 10.

The bag-like filter 28 (with the air tube 66 inserted through hole 73) is positioned horizontally, in surface to surface juxtaposition on the midregion of first sheet 12 such that the air tube 66 will pass upwardly, between the first 74 and second 76 rigidifying members, such that the upper end of the air tube 66 extends beyond the upper edge of the first sheet 12.

A non-stick material such as polytetrafluoroethylene (Teflon TM) or another object is positioned within the mouth 30 of the bag-like filter element 28 so as to prevent subsequent fusion or heat sealing, in that region, of the first sheet 12 to the second sheet 14 while permitting the outer edges of the filter 28 to become fused laterally to the first 12 and second 14 sheets, respectively.

The blood inlet tube 40 is positioned such that its upper end extends slightly above the lower edge of the first sheet 12, with the remaining length of the blood inlet tube 40 being aligned in its desired operative disposition. Similarly, the blood outlet tube 60 is positioned such that its upper end extends slightly above the lower edge of the first sheet 12 with the remaining portion of the blood outlet tube 60 being arranged in its desired operative disposition. Thereafter, the second or upper sheet 14 is laid in surface to surface juxtaposition on the first sheet 12, such that apertures ***64a*, *64b* and *64c* are all in appropriate alignment. By such arrangement, the bag-like filter element 28, rigidifying strips 74 and 76, a portion of the air vent tube 66 and the ribbed upper ends 41 and 61 of the venous inlet 40 and outlet 60 tubes are respectively sandwiched between the first sheet 12 and the second sheet 14**.

Figure 1:
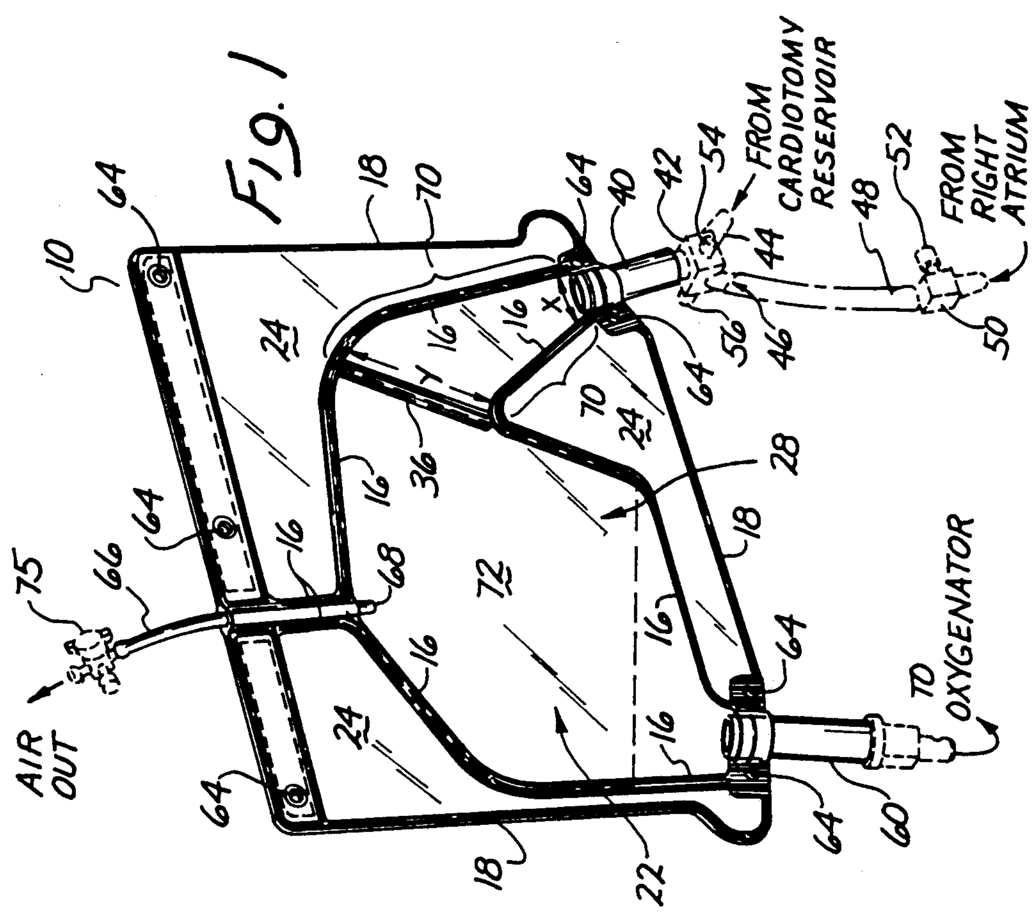
FIG. 1 is a perspective view of a venous reservoir of the present invention.
Figures 2, 5, 6:
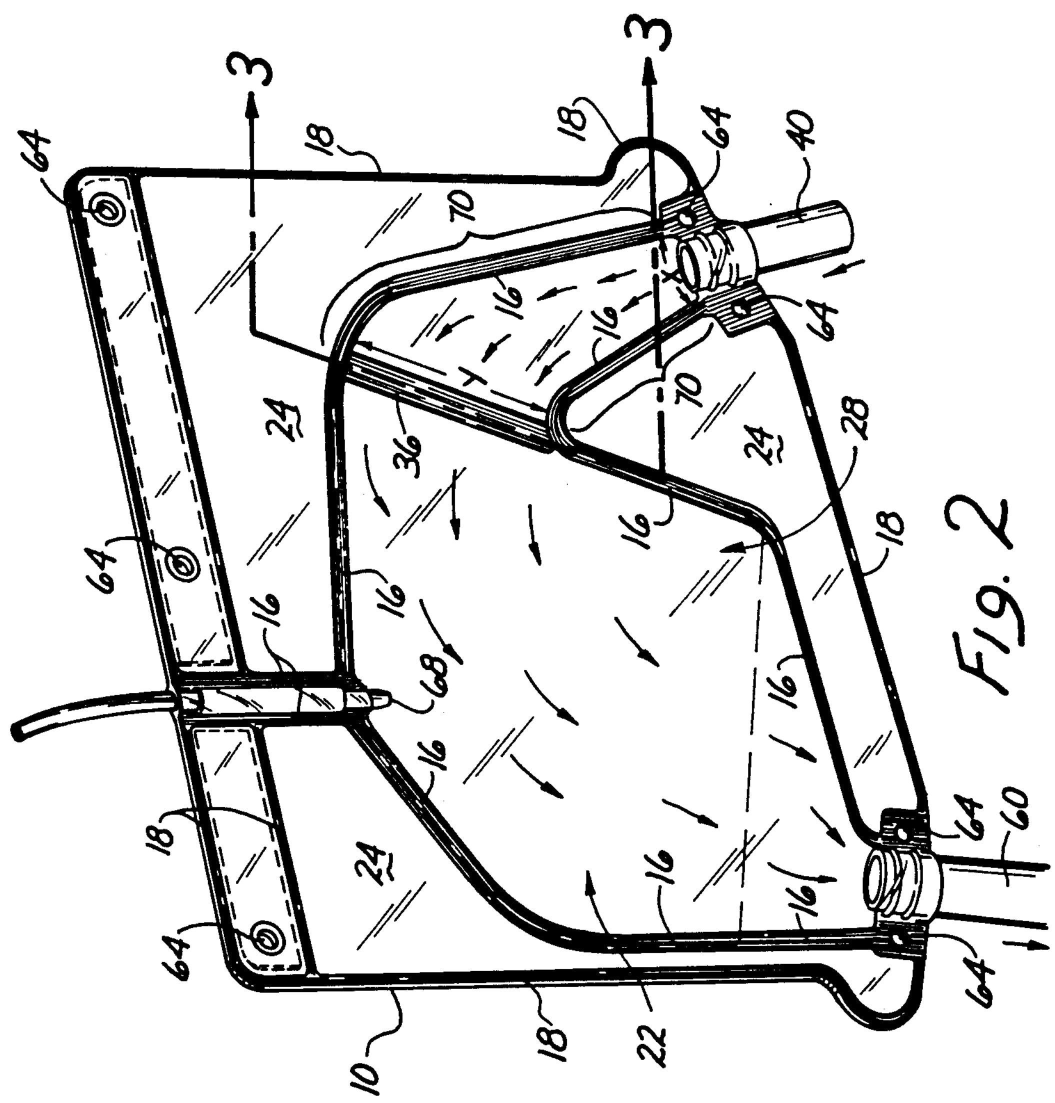
FIG. 2 is a perspective view of a venous reservoir of the present invention.
FIG. 5 is an end view of the filter component of a venous return reservoir of the present invention as taken from line 5—5' of FIG. 4.
FIG. 6 is an end view of the filter of a venous return reservoir of the present invention as taken from line 6—6' of FIG. 4.

Thereafter, a radio frequency or heat sealing device is compressively applied to the first 12 and/or second 14 sheets, to cause fusion and/or joinder of the first sheet 12 to the second sheet 14 in the regions of seams or boundaries 16 and 18. The fusion or sealing of the sheets 12, 14 along the inner boundary 16 will also serve to entrap and hold the outer edges of the filter element 28 in its operative location within the main chamber portion. Additionally, such heat or radio frequency sealing will serve to fuse the first and second sheets 12, 14 around hole 73 and around the base of the air outlet tube 66 so as to substantially prevent leakage of air and to firmly hold the air outlet tube 66 is position, as shown in FIGS. 1 and 2. Additionally, such heat or radio frequency sealing will firmly seal the first 12 and second 14 sheets to the upper ends 41 and 61 of the blood inlet 40 and blood outlet 60 tubes and will stamp or otherwise from ribs or ridges therein, as shown. Such ribs or ridges will minimize the likelihood that the tubes 40, 60 may be subsequently pulled out of the chamber 22 during use of the device 10.

Additionally, such heat or radio frequency sealing will also serve to fuse the first sheet 12 to the bottom side of the mouth 30 of filter element 28 and the top sheet 14 to the upper side of the mouth 30 of filter element 28, as indicated by seam 36. Thereafter, a pair of forceps, or other device may be utilized to reach into the chamber 22 through the venous inlet tube 40 and to extract the previously inserted non-stick strip (e.g. Teflon TM) or other object from within the mouth 30 of the filter element 28. This results in the mouth 30 of the filter element 28 remaining fully openable and expandable in accordance with the flow of venous blood through the reservoir 22.

iii. Operation of Illustrated Embodiment

In accordance with the invention, the embodiment shown in FIGS. 1–4 is initially mounted on a venous reservoir bag hanger device by pins or hangers inserted through aperture 64 so as to hold the reservoir 10 in operative position, without folds or creases formed therein. The cardiotomy inlet 44 is fluidly connected to the blood output port of an attendant cardiotomy filter device so as to provide a flow of filtered cardiotomy blood through cardiotomy inlet 44 into venous inlet tube 40. Additionally, the venous return inlet 48 is fluidly connected to the right atrium or vena cava of the patient so as to provide for a flow of fresh venous return blood into venous inlet line 40. The filtered cardiotomy blood and the venous return blood thus become commingled and/or mixed within the venous inlet tube 40 and/or the interior of the blood collecting space or chamber 22. Such combination or mixture of filtered cardiotomy blood and venous return blood will hereinafter be referred to as "venous blood".

After flowing through the venous inlet tube 40, the mixture of venous return and filtered cardiotomy blood will enter the inlet 70 of the chamber 22. As described above, the width and/or cross-sectional area x at the bottom end of the inlet 70 is less (e.g. tenfold less), than the width or cross-sectional area y at the top edge of the inlet 70. Such gradual widening of the inlet 70 provides for generally laminar flow of blood from the bottom edge x of the inlet 70 to the top edge y thereof. Such laminar flow within the inlet 70 will allow bubbles and entrained air within the blood to begin to separate and rise toward the highest point of the chamber, without the presence of unnecessary turbulence or eddy formation within the chamber.

Thereafter, the blood flows through the mouth 30 of the bag-like filter element 28, filling the main chamber 72 and, at some point, passing through the mesh walls of the bag-like filter 28 and subsequently out of the blood outlet tube 60, whereafter the blood is shunted to the attendant pump and/or oxygenator.

Air bubbles will rise to the top of the main chamber 72 and will coalesce and/or collect at the high point or peak of the chamber 22, near the base of air vent tube 68. As shown, it is preferable that the top edge of the main chamber be configured in a peaked or generally arched configuration or some other configuration whereby there is established a high point near the base 68 of the air vent tube to facilitate collection of air at the base of the air vent tube 68, rather than at other areas along the top edge of the main chamber 72. The stop cock 70 may then be fully or partially opened to permit periodic or continuous escape of gas or air from the upper region of the chamber 22.

The pliable construction of the reservoir 10 allows the walls of the chamber to spread apart and/or retract together in accordance with variations in the volume of blood contained within the chamber 22 at any given point in time. Thus, the flexibility of the chamber 22 allows the reservoir 10 to act as an accumulator or capacitance vessel such that an attendant pump (not shown) may pump blood from the blood outlet tube 60 at a fixed or varied rate, while the feed rate of blood through blood inlet tube 40 may occur at a fixed or varied rate, with the pliability of the chamber 22 providing sufficient capacitance or accumulation capability as to accommodate any resultant variations in the volume of blood contained within the chamber 22.

The foregoing description and the accompanying drawings were provided for purposes of describing an illustrative embodiment of the invention. Those skilled in the art will recognize that various modifications may be made to the above-described illustrative embodiment without deviating from the spirit and scope of the present invention. For example, the inner boundary 16 which still maintaining the desirable blood and gas flow dynamics of the chamber 22 as embodied in the present invention (e.g. the generally laminar flow of blood within the inlet 70 region of the chamber and the gas collecting shape of the top edge of the inner boundary 16). Additionally, the inlet region 70 of the chamber 22 may be configured differently from that shown in the drawings, while still maintaining the desirable fluid dynamics and minimization of turbulence as to facilitate separation and rising of bubbles entrained within the blood. Additionally, the filter 28 may be configured differently than that shown in FIGS. 1–4, or may be located only in a smaller portion of the chamber 22, thereby differing from that shown in the drawings, but still remaining within the scope of the present invention. Accordingly, it is intended that these modifications, and others, be included within the scope of the following claims.

What is claimed is:

1. A blood reservoir device comprising: a generally flexible blood collection chamber having;

(a) an inlet portion; and (b) a main portion;

said inlet portion and said main portion being fluidly connected to one another such that blood may pass therebetween;

a blood inflow tube fluidly connected to the inlet portion of the blood collection chamber;

a blood outflow tube fluidly connected to the main portion of the blood collection chamber;

at least one air vent tube fluidly connected to the blood collection chamber to vent air therefrom;

said collection chamber inlet portion having a first blood entry location where blood flows into the inlet portion and a second blood departure location where blood flows out of the inlet portion into the main portion of said collection chamber, said inlet portion being sized and configured such that the cross-sectional area of said inlet portion gradually increases from said first location to said second location so that blood flowing between the first location and the second location is generally laminar and free of excessive turbulence.

2. The device of claim 1 wherein said first location and said second location are separated by approximately 4½ inches and wherein the cross-sectional area of the said inlet portion at the first location is approximately 0.2 square inches and the cross-sectional area at said second location is approximately 2.0 square inches.

3. The device of claim 1 wherein the cross-sectional area of he inlet portion increases at a rate of about 0.4 $in^2/in.$, for each succeeding inch of travel between the first location and second locations.

4. The device of claim 1 wherein the inlet portion is generally conical in configuration.

5. The device of claim 1 wherein the inlet portion is formed in the configuration of a curved cone.

6. The device of claim 1 wherein the inlet portion is formed to have a generally elliptical cross-sectional configuration.

7. The device of claim 1 wherein the blood collection chamber further comprises an edge of generally peaked or curved configuration adjacent said air vent tube such that gas will collect at a high point of said peaked or curved configuration adjacent said air vent tube.

8. The device of claim 1 wherein the highest point of the blood collection chamber is located within the main portion of the chamber.

9. The device of claim 1 further comprising:

a filter element positioned within said blood collection chamber to collect and remove air bubbles from blood passing through the blood collection chamber.

10. The device of claim 9 wherein said filter element comprises a screen.

11. The device of claim 9 wherein said filter element comprises a soft mesh material.

12. The device of claim 9 wherein the filter element comprises a multiplicity of filtration pores, said filtration pores being from 20 to 200 microns in size.

13. The device of claim 9 wherein said filter element comprises a multiplicity of filtration pores, said pores having an average size of about 105 microns.

14. The device of claim 9 wherein said filter element is formed as a bag, having a mouth portion for receiving blood thereinto, said filter element being positioned such that said mouth is disposed the second location, such that blood flowing from the inlet portion into the main portion will enter the mouth of the bag-like filter element.

15. The device of claim 1 wherein the main portion of the collecting chamber is larger than the inlet portion of the collecting chamber.

* * * * *